United States Patent [19]
Walker et al.

[11] Patent Number: 5,902,304
[45] Date of Patent: May 11, 1999

[54] TELESCOPIC BONE PLATE FOR USE IN BONE LENGTHENING BY DISTRACTION OSTEOGENESIS

[76] Inventors: David A. Walker, 9 Banting Court, Thornhill, Ontario, Canada, L3T 7L7; Gurkan Altuna, 386 Glengrove Avenue W., Toronto, Ontario, Canada, M5N 1W6; Eric Freeman, 36 Weatherstone Cres., Willowdale, Ontario, Canada, M2H 1C2

[21] Appl. No.: 08/757,475

[22] Filed: Nov. 27, 1996

Related U.S. Application Data

[60] Provisional application No. 60/007,847, Dec. 1, 1995.

[51] Int. Cl.$^6$ .................................................. A61B 17/56
[52] U.S. Cl. .............................. 606/71; 606/57; 606/69; 606/70
[58] Field of Search ................................ 606/69, 70, 71, 606/105, 57, 58, 62, 63

[56] References Cited

U.S. PATENT DOCUMENTS

| | | |
|---|---|---|
| 3,976,060 | 8/1976 | Hildebrandt et al. . |
| 5,129,903 | 7/1992 | Luhr et al. . |
| 5,364,396 | 11/1994 | Robinson et al. . |

FOREIGN PATENT DOCUMENTS

| | | |
|---|---|---|
| 0 073 455 | 3/1983 | European Pat. Off. . |
| 0 450 075 | 10/1991 | European Pat. Off. . |
| 2 267 080 | 11/1975 | France . |
| 2 213 283 | 8/1973 | Germany . |
| 4007306 | 5/1991 | Germany ................................ 606/71 |
| 41 32 021 | 4/1993 | Germany . |
| 335797 | 3/1959 | Switzerland ............................. 606/71 |
| 1754085 | 8/1992 | U.S.S.R. .................................. 606/70 |

OTHER PUBLICATIONS

Oklund S.A., Prolo D.J., Gutienez R.Y., King S.E., "Quantitative comparison of healing in cranial fresh autografts and processed autografts and allografts in canine skull defects". Clin Orthop 205: 269–291, 1986.

Wolfe S.A., "Autogenous bone grafts versus alloplastic material in maxillofacial surgery", Clin Plast Surg 9:539–540, 1982.

Benoist M., "Experience with 220 cases of mandibular reconstruction", J Oral Maxillofac Surg 6:40–49, 1978.

Wolford L.M., Wardrop R.W., Hartog J.M., "Coralliac porus hydroxyapatite as a bone graft substitute in orthognathic surgery", J Oral Maxillofac Surg 45: 1034–1042, 1987.

Araujo A, Schendel S, Wolford L, Epker B., "Total maxillary advancement with and without bone grafting", J Oral Surg 63:849–858, 1978.

Horster W., "Experience with functionally stable plate osteosynthesis after forward displacement of the upper jaw", J Maxillofac Surg 8:176–181,1980.

Westwood R, Tilson H., "Complications associated with maxillary osteotomies", J Oral Surg 33:104–107, 1975.

Bell W, Levy B., "Healing after anterior maxillary osteotomy", J Oral Surg 28: 728–734, 1970.

Ilizarov G. Devyatov A, Kamerin V., "Plastic reconstruction of longitudinal bone defects by means of compression and subsequent distraction", Acta Chir Plast 22:32–46, 1980.

(List continued on next page.)

*Primary Examiner*—Michael Buiz
*Assistant Examiner*—Julian W. Woo
*Attorney, Agent, or Firm*—Burns, Doane, Swecker & Mathis, LLP

[57] ABSTRACT

The invention is a telescopic bone plate for distracting osteotomically separated bone sections. In a preferred embodiment, the telescopic bone plate consists of a top bone plate and a bottom bone plate longitudinally, laterally and vertically adjustable relative to each other and including a device for fastening the telescopic bone plate to bone. A telescopic member adjusts the relative positions of the top and bottom bone plate to each other. The telescopic member is actuated internally to the patient and may be actuated intraorally in one variation.

39 Claims, 8 Drawing Sheets

OTHER PUBLICATIONS

Paley D., "Current techniques of limb lengthening", J. Pediatr Orthop 8:73–91, 1988.

Sproul J.T., Price CT., "Recent advances in limb lengthening", Part I. Clinical advances. Orthop Rev 21:307–314, 1992.

Simard S, Marchant M, Mencio G., "The Ilazarov procedure: Limb lengthening and its implications", Phys Ther 72:25–34, 1992.

Orbay J.L., Frankel V.H., Finkle J.E., Kummer F.J., "Canine leg lengthening by the Ilizarov technique", Clin Orthop 278:265–273, 1992.

DeBastiani G, Aldegheri R, Renzi–Brivio L, Trivella G., "Limb lengthening by callous distraction (callotasis)", J Pediatr Orthop 7;129–134, 1987.

Kojimoto H, Yasui N, Goto T, Matsuda S, Yutaka S., "Bone lengthening in rabbits by callus distraction", J Bone Joint Surg Br 70:543–549, 1988.

Aldegheri R, Renzi–Brivio L, Agostini S., "The callotasis method of limb lengthening", Clin Orthop 241:37–45, 1989.

White S.H., Kenwright J., "The time of distraction of an osteotomy", J Bone Joint Surg Br 72:356–361, 1990.

Cattaneo R., Villa A, Catagni M.A., Bell D., "Lengthening of the humerus using the Ilizarov technique", Clin Orthop 250:117–124, 1990.

Iizariv technique, Clin Orthop 250:117–124, 1990. Villa A, Paley D, Catagni M.A., Bell D, Cattaneo R., "Lengthening of the forearm by the Ilizarov technique", Clin Orthop 250:125–137, 1990.

Moore H.M., Guzman–Stein G, Proudman T.W., Abbott AH, Netherway D.J., David D.J., "Mandibular lengthening by distraction for airway obstruction in Treacher–Collins syndrome", J. Craniofac Surg 5:22–25, 1994.

Tschakaloff A, Losken H, Mooney M, Sregel M et.al., "Internal calvarial bone distraction in rabbits with experimental coronal suture immobilization", J Craniofacial Surg 5:5 318–325, 1994.

Altuna, G., Walker, D.A., Freeman, E., "Rapid orthopedic lengthening of the mandible in primates by sagittal split osteotomy and distraction osteogenesis: A pilot study", *Int. J. Adult Orthod. Orthognath, Surg.,* 10:1, 59–64 (1995).

Altuna, G., Walker, D.A., Freeman, E., "Surgically assisted rapid orthodontic lengthening of the maxilla in primates—A pilot study", *Am. J. Orthodtofac. Orthop.,* 107:5, 531–536 (1995).

Altuna, G., Walker, D.A., Freeman, E., "Surgically assisted–rapid orthopedic lengthening of the maxilla in primates: Relapse following distraction osteogenesis", *Int. J. Adult Orthod. Orthognath. Surg.,* 10:4, 269–275 (1995).

Chin, M., Toth, B.A., "Distraction osteogenesis in maxillofacial surgery using internal devices: Review of five cases", *J. Oral Maxillofac. Surg.,* 54:45–49 (1996).

Costantino, P., Friedman, C.D., "Distraction osteogensis: Applications for mandibular regrowth", *Otolaryngol. Clin. North Am.,* 24:6, 1433–1443 (1991).

Costantino, P.D., Friedman, C.D., Shindo, M.L., Houston, G., Sisson, G.A., "Experimental mandibular regrowth by distraction osteogenesis: Long–term results", *Arch. Otolaryngol Head neck Surg.,* 119:511–516 (1993).

Costantino, P.D., Shybut, G., Friedman, C.D., Pelzer, H.J., Masini, M., Shindo, M.L., Sisson, G.A., "Segmental mandibular regeneration by distraction osteogenesis", *Arch. Otolaryngol Head Neck Surg.,* 116:535–545 (1990).

Gantous, A., Phillips, J.H., Catton, P., Holmberg, D., "Distraction osteogenesis in the irradiated canine mandible", *Plast. Reconstr. Surg.,* 93:1, 164–168 (1994).

Ilizarov, G.A., "The tension–stress effect on the genesis and growth of tissues", *Clinical Orthopaedics and Related Research,* 238: 249–281 (1989).

Karp, N.S., McCarthy, J.G., Schreiber, J.S., Sissons, H.A., Thorne, C.H.M., "Membranous bone lengthening: A serial histological study", *Ann. Plast. Surg.,* 29:1, 2–7 (1992).

Karp, N.S., Thorne, C.H.M., McCarthy, J.G., Sissons, H.A., "Bone Lengthening in the craniofacial skeleton", *Ann. Plast. Surg.,* 24:3, 231–237 (1990).

Komuro, Y., Takato, T., Harii, K., Yonemara, Y., "The histologic analysis of distraction osteogenesis of the mandible in rabbits," *Plast. Reconstr. Surg.,* 94:1, 152–159 (1994).

McCarthy, J.G., Schreiber, J., Karp, N., Thorne, C.H., Grayson, B.H., "Lengtheningthe human mandible by gradual distraction", *Plast. Reconstr. Surg.,* 89:1, 1–10 (1992).

McCarthy, J.G., Staffenberg, D.A., Wood, R.J., Cutting, C.B., Grayson, B.H., Thorne, C.H., "Introduction of an intraoral bone–lenthening device", *Plast. Reconstr. Surg.,* 96:4, 978–981 (1995).

Molina, F., Monasterio, F.O., "Mandibular elongation and remodeling by distraction: A farewell to major osteotomies", *Plast. Reconstr. Surg.,* 96:4, 825–840 (1995).

Paley, D., "Problems, obstacles, and complications of limb lengthening by the Ilizarov technique", *Clin. Orthop.,* 250, 81–104 (1990).

Snyder, C. Levine, G.A., Swanson, H.M., Browne, E.Z., Jr., "Mandibular lengthening by gradual distraction", *Plast. Reconstr. Surg.,* 51:5, 506–508 (1973).

TELESCOPIC BONE PLATE FOR USE IN BONE LENGTHENING BY DISTRACTION OSTEOGENESIS

CROSS REFERENCE TO RELATED APPLICATIONS

This application claims the benefit of U.S. Provisional Application Ser. No. 60/007,847, filed Dec. 1, 1995, which is incorporated by reference herein in its entirety.

FIELD OF THE INVENTION

The invention relates to a device for lengthening bone by distraction osteogenesis. In particular, the device is an internal telescopic bone plate with a longitudinally actuable means to adjust the relative separation of top and bottom bone plates in order to distract bone.

BACKGROUND OF THE INVENTION

Thousands of children world-wide exhibit cranio-facial defects, and the treatment of these deformities is challenging. Various surgical techniques are used to treat these problems. However, clinical advancements in facial bone reconstruction have been limited. Presently, we still depend largely on autogenous or autologous bone grafts for the reconstruction of the non-stress bearing as well as the stress-bearing facial skeleton. These grafts are difficult to contour, are available only in limited quantities, and can undergo significant graft resorption. Synthetic materials such as hydroxyapatite or carbon-based polymers have proved useful in aesthetic augmentation of the facial skeleton but they frequently lack the structural stability necessary for major head and neck reconstruction. Furthermore, these synthetics have proved to be uniformly inadequate for the reconstruction of stress-bearing bone such as the mandible (1,2,3,4,5,6). In addition, complications occur subsequent to surgery, such as devitalisation of teeth, partial or complete loss of an osteotomized segment and bone graft failure (7,8,9,10). Distraction of an osteogenesis has been used in recent years to overcome the problems with the surgical techniques discussed above. In this application, the term "distraction osteogenesis" is the method of growing new bone by stretching pre-existing bone. This technique, which was first described by Ilizarov et. al. (11), involves surgically fracturing the bone with minimal disruption of its periosteal and endosteal envelope. After the surgery, a waiting period of 7 to 10 days allows new bone cells to populate the area. At the end of the waiting period, the bone on each side of the fracture site is stretched by various mechanical means at a rate of 1.0 mm per day (11–16).

Currently, distraction osteogenesis has been clinically applied on a widespread basis within orthopedic surgery. It has been used for the replacement of segmental defects, the treatment of fracture non-unions and the elongation of shortened extremities. This technique has also been used within orthopedic surgery for the correction of traumatic congenital deformities in both the long bones of the extremities and the smaller bones within the hands and feet. (17–20)

Although distraction osteogenesis has been applied to orthopedic problems on a widespread basis, it has been used for facial skeletal reconstruction on an experimental basis only. Clinical experience in orthopedic surgery indicates that bone created by distraction osteogenesis is structurally stable and that it should be able to withstand the shear and torsional stresses that the mandible is subjected to during mastication. The main disadvantage of using distraction osteogenesis for facial skeletal reconstruction is that the orthopaedic mechanical devices are too large to be applied within the craniofacial systems.

In orthopedics, numerous pin and ringed fixators are available for limb lengthening, including those taught by Wagner, De Bastiani (Orthofix), Ilizarov, Monticelli-Spinelli and Acefisher. All of these mechanical devices are external to the skin (20,21,22,23). The problems reported in the literature with respect to these devices are as follows (24):

1. External mechanical devices are large and cumbersome and interfere with the patient's daily lifestyle.
2. Pin loosening and pin-tract infection results in the development of soft tissue inflammation/infection at the external site and this leads to bone infection.
3. Neurovascular injuries occur due to pin placement.

The first attempt to apply the principles of distraction osteogenesis within the craniofacial system to lengthen the mandibular body was by Snyder et al. (36) in 1973. An external (outside the skin) screw-driven device attached with bicortical pins was used.

In 1990, Karp (32) and his colleagues used an external (outside the skin) bone-lengthening device at the mandibular expansion site. The device was comprised of a standard external fixator with two double-pin holders and a bolt at one end that allowed calibrated distraction or compression of the pins (Howmedica Corp., Rutherford, N.J.).

In 1992, McCarthy (30) and his co-workers used this external (outside the skin) device to lengthen the mandible on children with congenital growth defects.

Also in 1992, Luhr et al. described an extendable bone plate to fix the fracture of small bones (U.S. Pat. No. 5,129,903). The Luhr device exhibits a lack of sectional modulus to support compressive load and the self-locking feature is questionable. Testing with respect to technical specifications and animal or clinical studies has not been disclosed.

In 1995 Molina and Monasterio (40) in Mexico City reported on clinical applications of external pin distraction osteogenesis in the mandible in 106 patients. The mean age of patients was 8 years of age and surgical technique utilized was intra oral corticotomy with placement of two percutaneous pins. The distraction appliance was activated extra orally. The mean follow up was 19 months and x-rays were taken at selected intervals. In their patient group all patients received bite back orthodontic therapy post operatively.

These authors report temporomandibular joint pain in the unaffected side with evidence of bony remodelling of the non-treated temporomandibular joint. Skin scars were noted for all patients but the authors claim no infection, fractures, but did relate skin inflammation and three patients requiring antibiotic therapy. These authors did accomplish distraction osteogenesis in the mandible with no reported relapse. There is poor documentation regarding long term radiographic follow up. There is no comment on neuro sensory changes in the inferior alveolar nerve or discussion regarding devitalization of tooth roots and tooth buds due to pin placement. Additionally all patients received orthodontic bit block therapy which may have contributed significantly to long term stability of the distracted bony segments.

In 1995 McCarthy et al. (41) reported on experimental development of an intra oral mandibular distraction appliance. This was applied to ten mongrel dogs with distraction osteogenesis. Pins were placed percutaneously but stabilized to an intra oral appliance. The appliance was bulky and crude and had minimal stabilization with two pins per segment of the mandible. Additionally the appliance did not have the multi directional capacity of adjustment in many vectors required for distraction osteogenesis of the mandible.

In 1996 Chin and Toth (42) reported on distraction osteogenesis utilizing internal devices in patients. An internal device was fastened to the mandible via screws and was distracted via trans oral activation. This technique was utilized in three patients. Premature consolidation of bone was noted in two patients and one patient had significant relapse. The authors comment that improved stability of attachment on the device to bone was needed. This appliance also did not have multi directional capabilities of controlling the vector of distraction of the mandible. The authors also report of breakage of one of their expansion screws which required further surgery to remove and replace this. Bilateral appliance was also used to advance the mid face and maxilla but was activated through a percutaneous screw which would leave an unsightly scar.

U.S. Pat. No. 5,364,396 to Robinson et al discloses an implantable distraction device which is proposed to permit gradual bone distraction between osteotomically separated bone sections. This device is made up of welded components and permits direct control of the bony segments. It is proposed to have a low profile, although its size and other specifications are not disclosed. It is not telescopic. The device has one force vector and there is no disclosure with respect to testing.

The Robinson et al device is implanted subcutaneously, however, actuation is extraorally via a percutaneous (through unbroken skin) port projecting outward through the skin. The percutaneous site would be subject to pin-tract infection and scar formation as the actuation port would project through the skin during the actuation and retention periods. As parts of Robinson's device are welded together, the device lacks the compressive strength needed for an effective distractor. Furthermore, as Robinson's device is not telescopic, it lacks a double displacement path and results in a larger device.

Tschakaloff (39) and his colleagues used a subperiosteal calvarial distractor for the correction of craniosynostosis in rabbits in 1994 (Medicorn Micro Systems, Tuttligen, Germany).

All the extra-oral devices used to date to conduct distraction osteogenesis is the craniofacial system have the following problems, as reported in the literature: (25–37).

1. Due to the fact that the activation mechanisms of these devices are outside the skin, the pins cut the skin during the activation procedure, resulting in the formation of scar tissue.
2. The pins used in these devices are unstable and weak. There have been a number of reports of pin loosening, resulting in relapse.
3. Pin instability increases as the amount of distraction to be carried out increases. Pin instability also increases as the length of the healing period increases.
4. Because the devices are extra-oral, the pin-tract infection that has been reported in orthopedic cases has also been observed with the devices used in the craniofacial system.
5. The extra-oral and cumbersome nature of these devices along with the formation of scar tissue has negative effects on patient co-operation and psychology.

Thus, a need exists for a distraction device that is stable, easy to activate and completely tissue-covered.

SUMMARY OF THE INVENTION

This invention satisfies those needs. The invention is a telescopic bone plate for distracting osteotomically separated bone sections. The plate consists of a top bone plate and a bottom bone plate longitudinally adjustable relative to each other and the device also includes means for fastening the telescopic bone plate to bone. The telescopic bone plate also has a telescopic means located between the top and bottom bone plates to adjust their positions relative to each other. The telescopic means is actuated internally to the patient. The telescopic bone plate may also be actuated intraorally.

In another embodiment, the telescopic bone plate for distracting osteotomically separated bone sections, of a top bone plate and a bottom bone plate adjustable relative to each other in at least one of a medial lateral direction, a superior inferior direction and an anterior posterior direction. This embodiment includes means for fastening the telescopic bone plate to bone, and at least one displacement means to adjust the relative positions of the top and bottom bone plate to each other. The displacement means is actuated internally to the patient.

The displacement means may also be actuated intraorally.

The telescopic means can be actuated on a plane that is substantially the same plane as a plane of the top bone plate or bottom bone plate. The displacement means may be a telescopic means which is actuated in a medial lateral plane. The displacement means can also be a telescopic means which is actuated in a superior inferior plane. In another variation, the displacement means is a telescopic means which actuates the top bone plate and bottom bone plate in an anterior posterior direction.

The displacement means of the telescopic bone plate may be actuated in a medial lateral plane. The displacement means may also be actuated in a superior inferior plane. In another variation, the displacement means actuates the top bone plate and bottom bone plate in an anterior posterior direction.

In one embodiment, the telescopic bone plate consists of a top panel and the bottom bone plate further comprises a bottom panel, wherein the top panel overlays the bottom panel and wherein the telescopic means is located between the top panel and the bottom panel.

After implantation the bone plate is completely covered with tissue of a patient. The telescopic bone plate also has a casing for the telescopic means of the bone plate.

In a preferred embodiment of the invention, the telescopic means is a thread screw assembly. The thread screw assembly has a hexagonal socket and is actuated by a hexagonal key. The thread screw assembly can be actuated intraorally using a control means located outside a patient's body. The thread screw assembly may be actuated internally to the patient using a control means located outside a patient's body.

In other preferred embodiment of the invention, the displacement means is a Jack screw assembly. The Jack screw assembly has a hexagonal socket and is actuated by a hexagonal key. The Jack screw assembly is actuated intraorally using a control means located outside a patient's body. In a preferred embodiment, the Jack screw assembly is actuated internally to the patient using a control means located outside a patient's body.

The telescopic bone plate may be made of stainless steel. One embodiment of the invention has a compressive strength of at least 1,290N. The profile of the telescopic bone plate can be less than 6 mm.

The bottom bone plate and the top bone plate may be inclined relative to the other. There may also be one or more slits between the holes to facilitate the contouring and fastening of the bone plate to bone.

The adjustable distance between the top and the bottom bone plate in one variation is at least 10 mm.

The invention includes a method of growing bone using the telescopic bone plate. The invention also includes a method of growing craniofacial bone using the telescopic bone plate of claim 1 or claim 2.

In a variation of the device, the telescopic means or displacement means is actuated by a motor.

DETAILED DESCRIPTION OF THE INVENTION

In order to overcome the problems in the prior art which are described above, Altuna, Walker and Freeman (37) used the first intra-oral distraction device to lengthen the mandible by using the principles of distraction osteogenesis and sagittal split osteotomy in primates.

A distractor was fabricated from a Glen-Ross screw with an opening capacity of 13 mm. The screw was soldered between two mini stainless steel bone plates. The bone plates were adjusted so that the Glen-Ross screw was at the same level as the mandibular occlusal plane. The posterior part of the screw was located 2 to 3 mm. from the gingival (gum) tissues and the anterior part was located 4 to 5 mm. from the gingival tissues. This was done to produce a force vector that would prevent the lateral displacement of the mandibular condyles (jaw joint). Each bone plate was fixed to both right and left proximal and distal mandibular segments by six self-tapping bicortical screws, and the surgical sites were closed with 4-0 gut sutures.

This device was stable during both the experimental and post-retention periods. There was no infection or scar tissue formation. The device was easy to activate and was tolerated well by the animal. Its construction made it possible to control the activation forces on two planes, sagitally and laterally. Histological analysis of the temporomandibular joints and the surgical site at the end of the experiment indicated that bone was deposited at the surgical site and that there was no joint pathology.

Although this intra-oral distraction device was superior to the extra-oral devices currently on the market, a distractor which would be completely covered by tissue would prevent infection and would also have the advantage of being more easily tolerated by the patient both in terms of comfort and aesthetics. With this in mind, a telescopic bone plate was developed that was totally tissue-covered. The bone plate was used to lengthen the mandible (lower jaw) of primates by distraction osteogenesis. The bone plate could be used to lengthen any other bone in the body.

The telescopic bone plate consists of top and bottom bone plates integrated with a telescopic means, which in a preferred mode of the invention, is a thread screw assembly. In this mode, a 5-44-UNF thread screw is contained within a top screw casing and a bottom screw casing. The 5-44UNF thread screw is a type of screw which includes a thread at each of the ends of its shaft. In an alternative embodiment, the casing for the telescopic means is a unitary screw casing.

The top bone plate is an extension of the top panel and the bottom bone plate is an extension of the bottom panel. In a variation of the device, the bottom panel and the top panel may be inclined relative to each other, creating an offset step. Slits may also be made in the top or bottom bone plates to allow for contouring of the plates to fit a curved bone surface.

An alternate embodiment of the invention includes an extended bone plate so that more screws can be placed posteriorly and anteriorly to increase stabilization of the device.

A preferred embodiment of the invention has additional components to permit activation of the device in multiple directions. These components allow modification of the vector of distraction of the appliance in a medial lateral plane and a superior inferior plane. Modifying the vector of distraction varies the path along which osteogenesis occurs by changing the direction and final position of the top bone plate and the bottom bone plate. This is particularly important in establishing final occlusion when distracting the mandible. Such precise control over the telescopic bone plate ensures optimal bone growth in the patient. This embodiment has an anterior adjustable screw oriented in a medial lateral plane to adjust the relative positions of the top and bottom bone plates. This screw is actuated through a small anterior incision in the mucosa. A posterior adjustable screw may be oriented in a superior inferior plane to adjust the relative positions of the top and bottom bone plates. This screw is actuated through a small posterior incision in the mucosa.

The hexagonal surface of the 5-44UNF thread screw comprises a socket which may be actuated with a standard hexagonal key. Each rotation of the screw produces a 1.1 mm expansion of the device. In alternative embodiments, the height and width of the telescopic bone plate may be varied to change the compressive load against the muscles of mastication. As well, the depth of the hexagonal socket may be altered for ease of actuation with a hexagonal key.

This telescopic bone plate is small enough to be used in the treatment of children with craniofacial defects. It can be surgically placed, covered by the oral mucosa, actuated through windows in the mucosa and completely covered and retained after actuation. The device enables the patient to well tolerate distraction of the bone.

The Advantages of this telescopic bone plate are:

1. Stability: the top and bottom bone plates of the device can be easily contoured to the surface of the bone. These bone plates are attached to the bone using monocortical and bicortical screws. All of these characteristics make the device more stable.
2. Ease of Actuation: The actuation mechanism of this telescopic bone plate makes it possible to control the actuation forces in three planes, sagitally, laterally and superior-inferior.
3. Completely tissue-covered: The device is totally tissue-covered after its implantation for a period (preferred period is 7 days). During the subsequent actuation period, a small 1 to 2 mm. opening is made for the insertion of the hexagonal key. Immediately after the actuation period, this opening heals by secondary intention. Thus, the device is totally tissue-covered during both the healing and retention periods. This characteristic of the telescopic bone plate is superior to any extra-oral appliance being used in animal or clinical models in preventing infection, in creating better stability of the device, and in incurring better patient acceptance.
4. Capability of screw: The thread screw assembly is uniquely constructed in that it has the capacity to expand beyond the capability of any screw currently on the market.
5. Multi direction activation: The anterior and posterior vector adjustment screws allow fine tuning of the direction of the displaced osteotomy segments in three planes of space.
6. Scale-up: The size of this telescopic bone plate can easily be increased to be used outside the craniofacial system in other parts of the body.
7. Remote control: The construction of the telescopic bone plate will allow the use of a miniaturized motor to actuate it, through the use of remote control. This allows the use of the device in areas of the craniofacial system that are not accessible for outside actuation through the use of an actuation key.

Several embodiments of the invention are described herein. We provide a number of variants of the invention to illustrate the various ways of practicing the invention. Four preferred embodiments of the invention are described below.

First Embodiment of the Invention

The telescopic bone plate described here has direct control of the bony segments. The top and bottom panels are integrated into the thread screw assembly with no welded components and give the device a very low profile (height of approximately 5.175 mm). The telescopic bone plate is telescopic whereby one unit of travel can be achieved by adding only half of the unit to the overall body length. The dove-tail interlocking track design is unique allowing for smooth operation and lateral stability. The bone plates can be customized to suit the surgical site and all specifications are disclosed, including a compressive strength of 1,290N. The device possesses three force vectors, sagittal, lateral and superior-inferior and was tested successfully in primates.

In this embodiment, the telescopic bone plate is implanted intraorally and is actuated intraorally via a window in the mucosa of the mouth. The hexagonal surface of the 5-44UNF thread screw is only exposed for the actuation period (10 days). The window is allowed to heal after actuation. There is no risk of pin-tract infection or scar formation.

Figure 1:
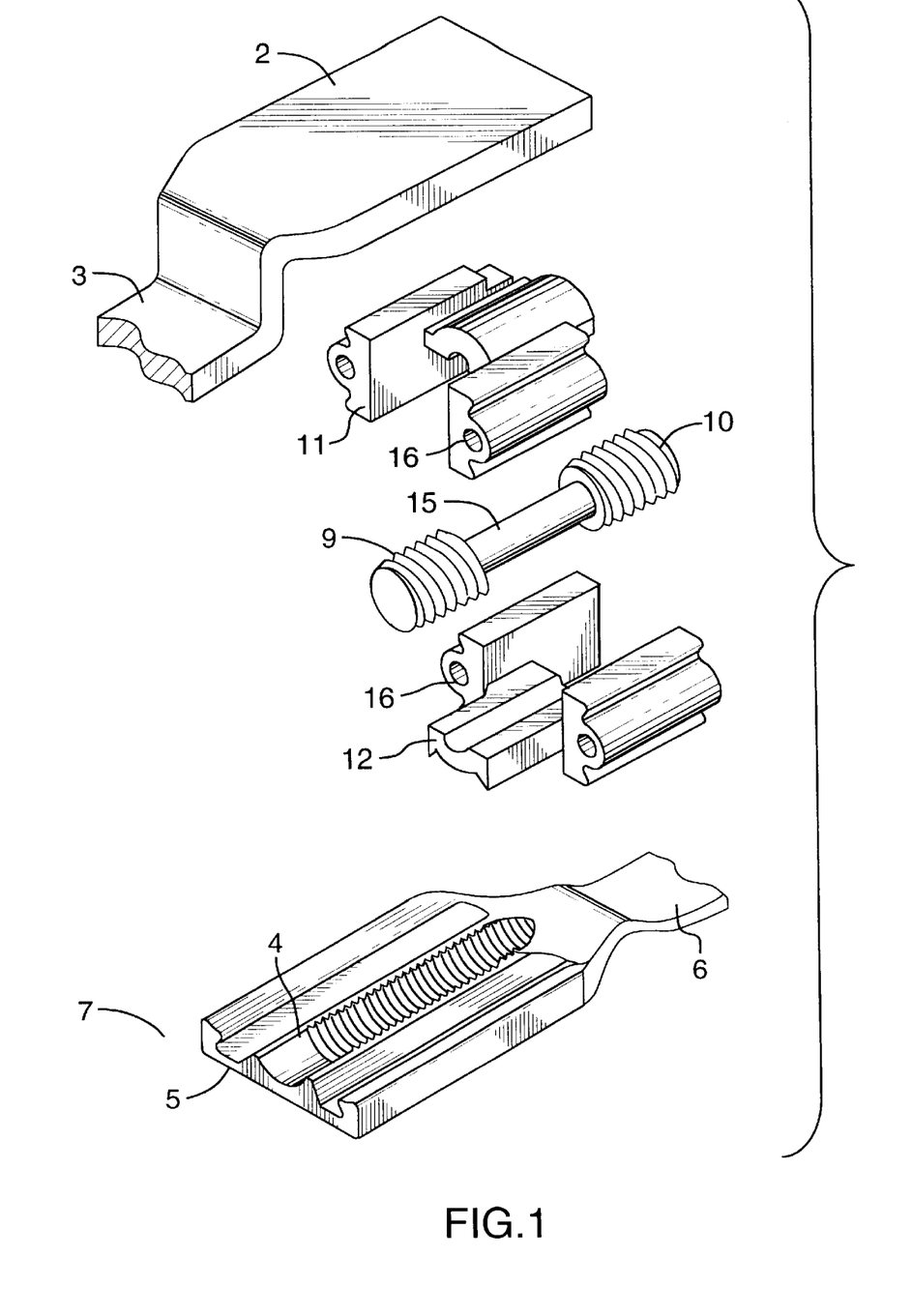
FIG. 1 is an exploded perspective view of the first embodiment of the telescopic bone plate.
Figure 4:
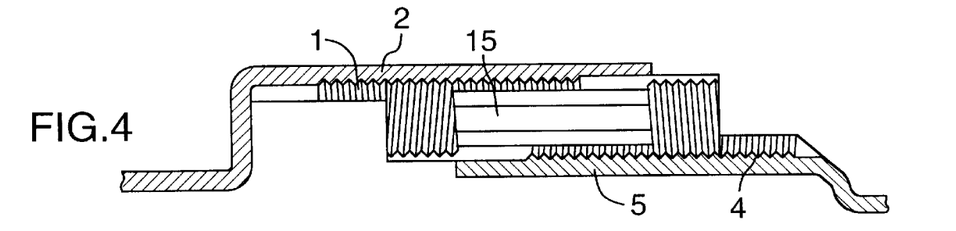
FIG. 4 is a section of a side view of the first embodiment of the telescopic bone plate.
Figure 5:
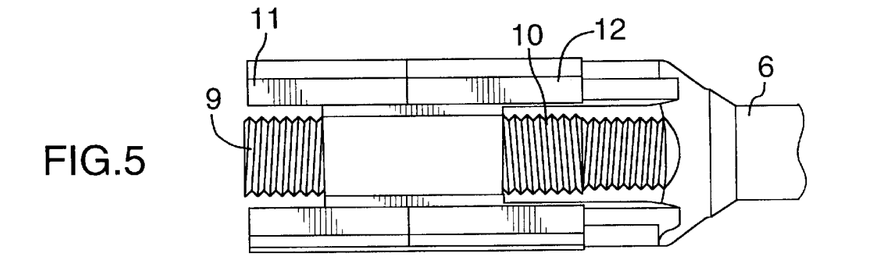
FIG. 5 is a plane view (left half removed) of the first embodiment of the telescopic bone plate.
Figure 6:
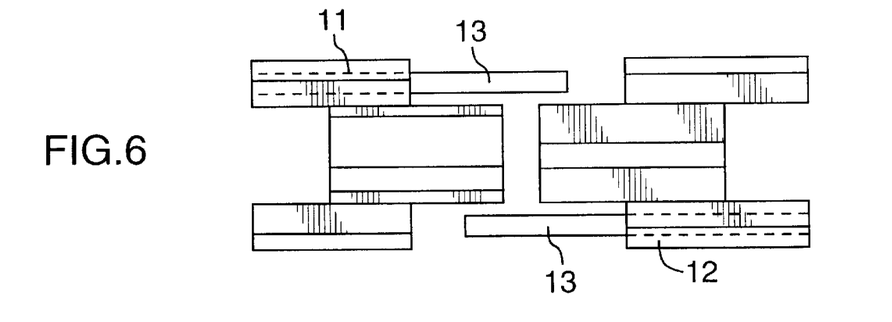
FIG. 6 is an exploded view of the screw casings of the first embodiment of the telescopic bone plate.

FIG. 1 shows the telescopic bone plate which consists of a top thread 1, a top panel 2, a customized top bone plate 3 integrated into the top panel; a bottom thread 4, a bottom panel 5, and a customized bottom bone plate 6 integrated into the bottom panel. The top bone plate 3 and the bottom bone plate 6 are depicted in cut-away form for purposes of FIGS. 4 and 5. FIG. 8 shows a typical top bone plate 3 and bottom bone plate 6. The shape of the top and bottom bone plates 3, 6 may be adjusted as needed and does not limit the scope of this invention. The top and bottom panels 2, 5 of the telescopic bone plate as well as the top screw casing 11 and the bottom screw casing, 12 employ a specially shaped "dove-tail" interlocking design 7 (FIGS. 1, 7), to ensure smooth operation and lateral stability. There are strategically located counter-sunk holes 8 on each of the top bone plate 3 and the bottom bone plate 6, which can be modified to suit the surgical site (FIG. 8). The degree of relative separation of the top and bottom bone plates 3, 6 is controlled by a longitudinally actuable telescopic means. In this preferred embodiment, the telescopic means is a thread screw assembly. The thread screw assembly contains a 5-44-UNF thread screw 15 which is threaded at both ends 9, 10 (FIGS. 1, 4, 5)). The 5-44UNF thread screw 15 is retained in a top screw casing 11 and a bottom screw casing 12, which are locked together by a pair of dowel pins 13 through holes 16 in the top screw casing 11 and holes 16 in the bottom screw casing 12 (FIGS. 1, 6).

Figure 2:
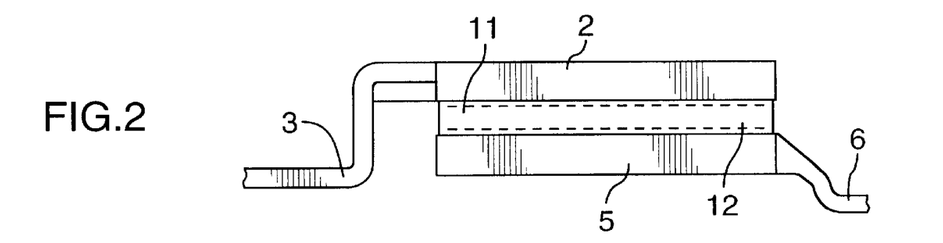
FIG. 2 is a side elevation closed view of the first embodiment of the telescopic bone plate.
Figure 3:
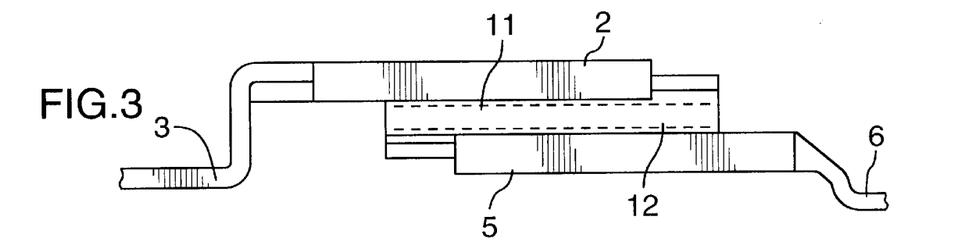
FIG. 3 is a side elevation open view of the first embodiment of the telescopic bone plate.
Figure 7:
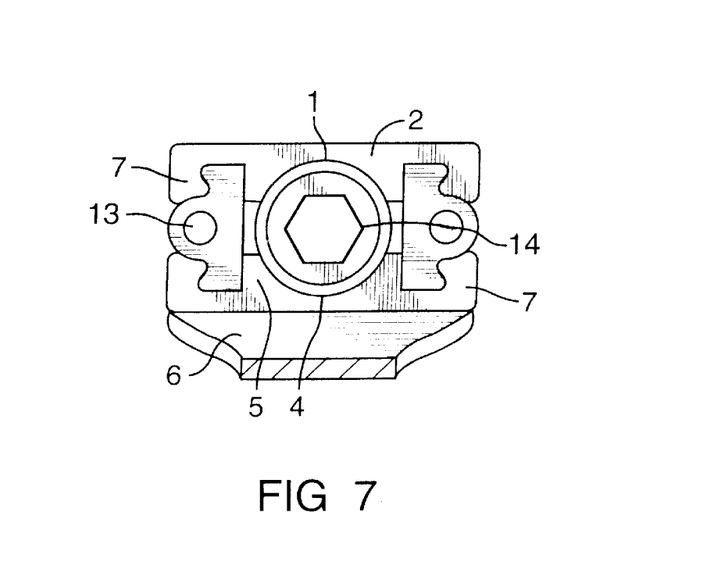
FIG. 7 is an end view of the assembly of the first embodiment of the telescopic bone plate.
Figure 8:
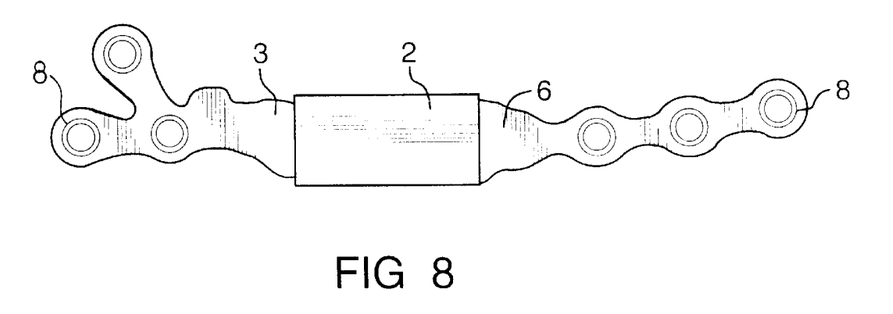
FIG. 8 is a plan view of the first embodiment of the telescopic bone plate.

A hexagonal socket 14 is located at the end of the 5-44UNF thread screw 15 for actuation purposes (FIGS. 1, 7). Upon actuation, the top and bottom panels 2, 5 along with integrated bone plates 3, 6 slide in opposite directions and by the same amount of travel distance producing a telescopic result. This causes the fractured bone segments to move apart (distract). FIG. 2 shows the telescopic bone plate in a closed position, where the top and bottom bone plates are not separated. Upon actuation of the telescopic bone plate, the top and bottom bone plates are separated, as shown in FIG. 3.

Actuation is by using a standard hexagonal key (described in more detail below).

Second Embodiment of the Invention

Figure 9:
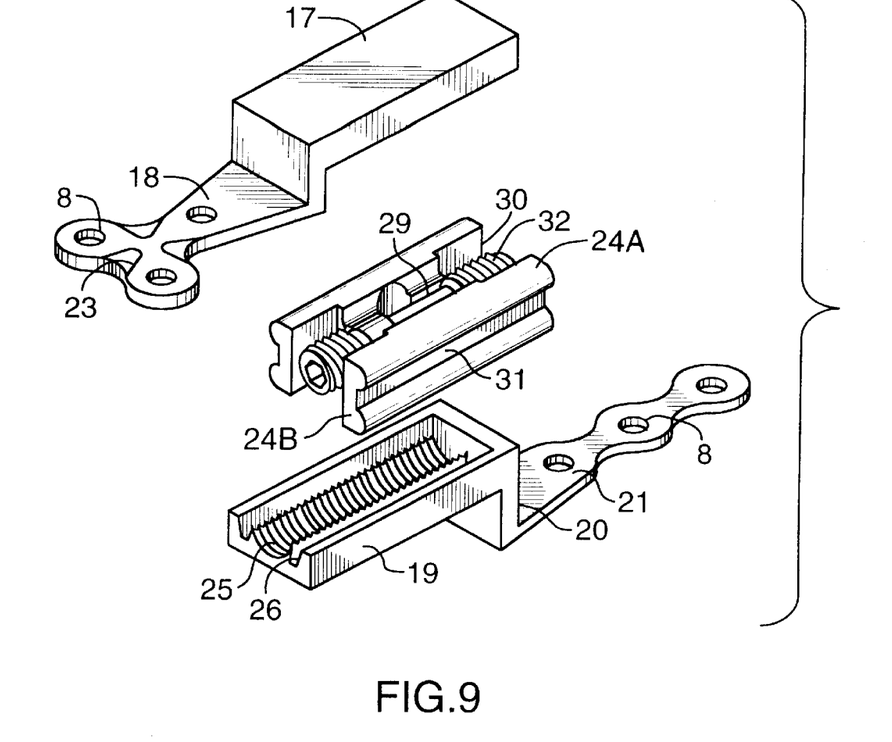
FIG. 9 is an exploded perspective view of the third embodiment of the telescopic bone plate.

A second commercial variation was developed and fabricated. This variant is similar to the first embodiment and includes changes in the design such as an addition of 1 mm in both width and height of the telescopic bone plate. This results in a higher compressive load against the muscles of mastication. As shown in FIG. 9, in one embodiment, the angle between the top panel and the top bone plate is acute; the angle between the bottom panel and bottom bone plate is obtuse. This results in an offset bone (step) of 2 mm. This maximizes the frontal vector of the resultant force and enables easier access to the hexagonal surface for actuation. The depth of the hexagonal socket is 3 mm. This ensures definitive placement of the standard hexagonal key. The metal between the counter-sunk holes in the top and bottom bone plates may be slit. This makes contouring the bone plate to the surgical site easier. There are three strategically located counter-sunk holes on each of the top and bottom bone plates disclosed herein and these can be modified to suit the surgical site. All of these features were also incorporated into the third embodiment of the invention and are illustrated in figures depicting that embodiment, discussed below.

Third Embodiment of the Invention

Figure 10:
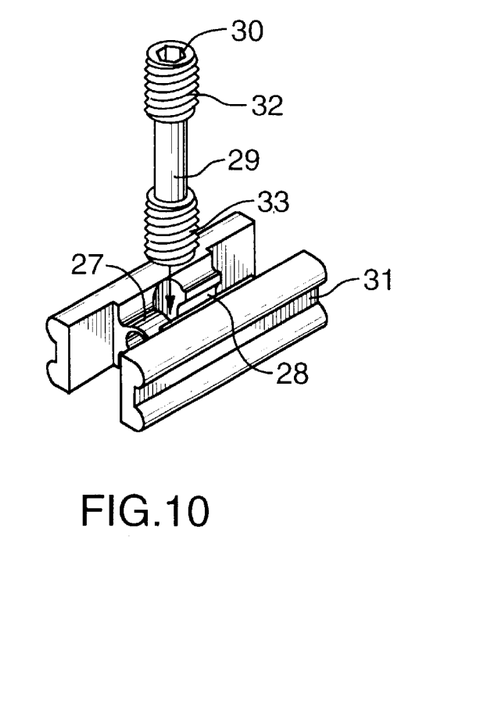
FIG. 10 is a perspective view of the unitary casing an the 5-44UNF thread screw of the third embodiment of the telescopic bone plate.
Figure 11:
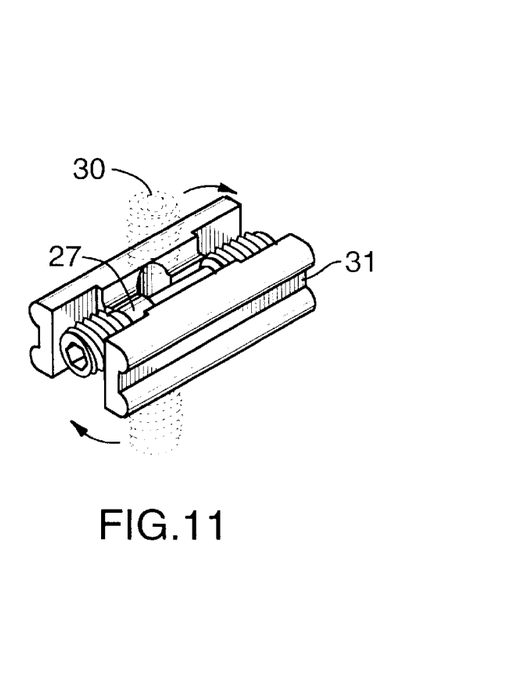
FIG. 11 is a perspective view of the unitary casing and the 5-44-UNF thread screw of the third embodiment of the invention. This view shows the insertion and seating of the 5-44UNF thread screw in the unitary casing.

A third embodiment of the invention was developed and fabricated, as shown in FIGS. 9–11. As well as the additional 1 mm in both width and height of the telescopic bone plate, there is an offset bend (step) 20 in the front bone plate of 2 mm, 3mm deep hexagonal surface 30 and slits 23 in the metal between the holes in the back bone plate. The internal geometry of the thread screw assembly is re-engineered (FIGS. 10, 11). It includes a unitary screw casing 31 instead of a two piece casing. This unitary screw casing 31 contains the 5-44-UNF thread screw use din the second embodiment. The screw casing 31 is easier to manufacture than the screw casing of the first and second embodiments of the invention. This is because the unitary screw casing 31 is constructed from one piece instead of two and it is not held together by dowel pins. The third embodiment of the telescopic bone plate consists of a top panel 17 with threads integrated into a customized top bone plate 18; a bottom panel 19 with threads 25 with a 2 mm step (offset) 20, integrated into a customized bottom bone plate 21. There are strategically located counter-sunk holes 8 on each of the top and bottom bone plates which can be modified to suit the surgical site. The panel track of the top panel 17 receives the unitary screw casing track 24A. The panel track 26 of the bottom panel receives the unitary screw casing track 24B. In this preferred embodiment, the unitary screw casing 31 contains the 5-44UNF thread screw 29 which is threaded at both ends 32, 33 (FIG. 10). The 5-44UNF thread screw 29 is retained by top brackets 27, and bottom brackets 28 of the unitary screw casting 31 (FIG. 11). A 3 mm hexagonal socket 30 is located at the end of the 5-44UNF thread screw 29 for actuation. Actuation is by using a standard hexagonal key which is inserted into the hexagonal socket 30 and turned. Upon actuation, the top panel 17 and the bottom panel 19 slide longitudinally in opposite directions, producing a telescopic result. This increases the separation between the top bone plate 18 and the bottom bone plate 21 which causes the fractured bone segments to move apart (distract). Gradual separation permits osteogenesis to occur.

Fourth Embodiment of the Invention

Figure 12:
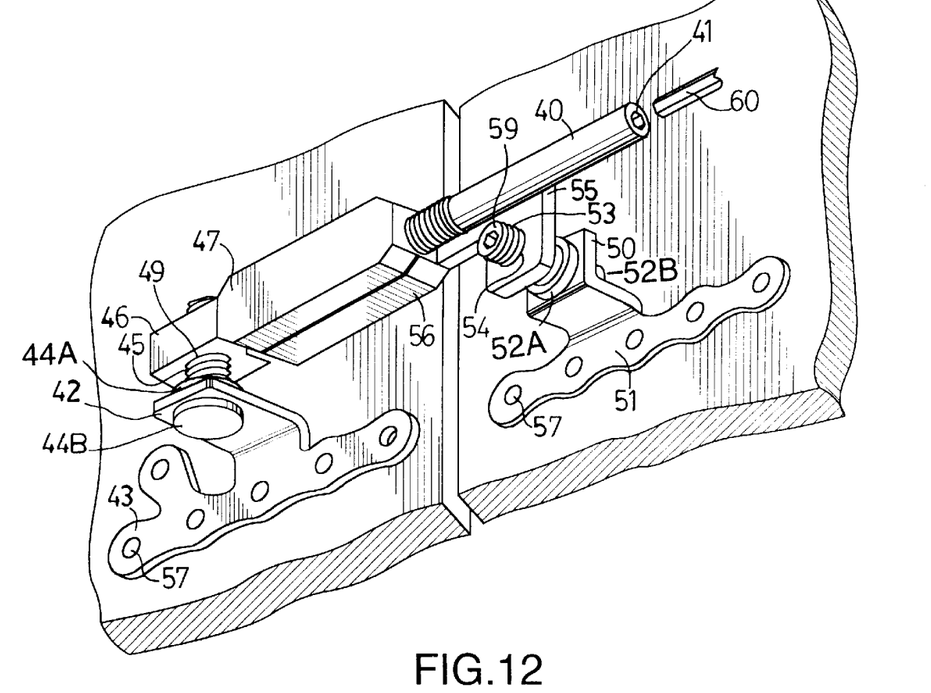
FIG. 12 is a perspective view of the fourth embodiment of the telescopic bone plate fixed at an osteotomy (surgical fracture of the bone) site.
Figure 13:
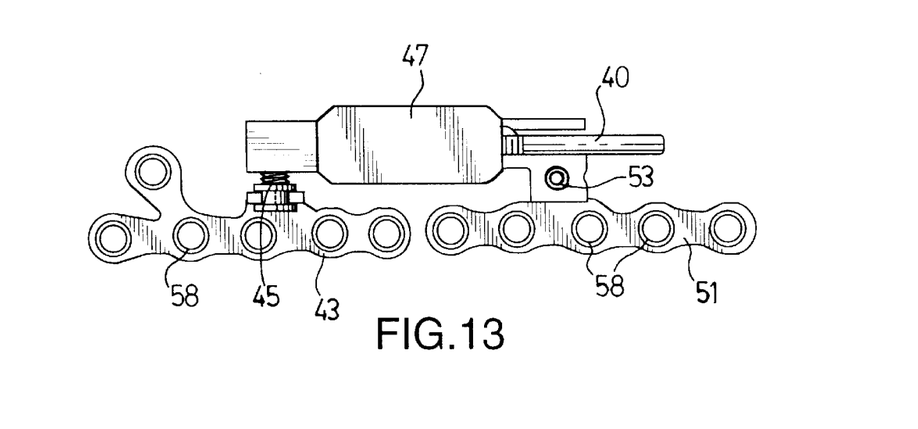
FIG. 13 is a plan view of the fourth embodiment of the telescopic bone plate.
Figure 14:
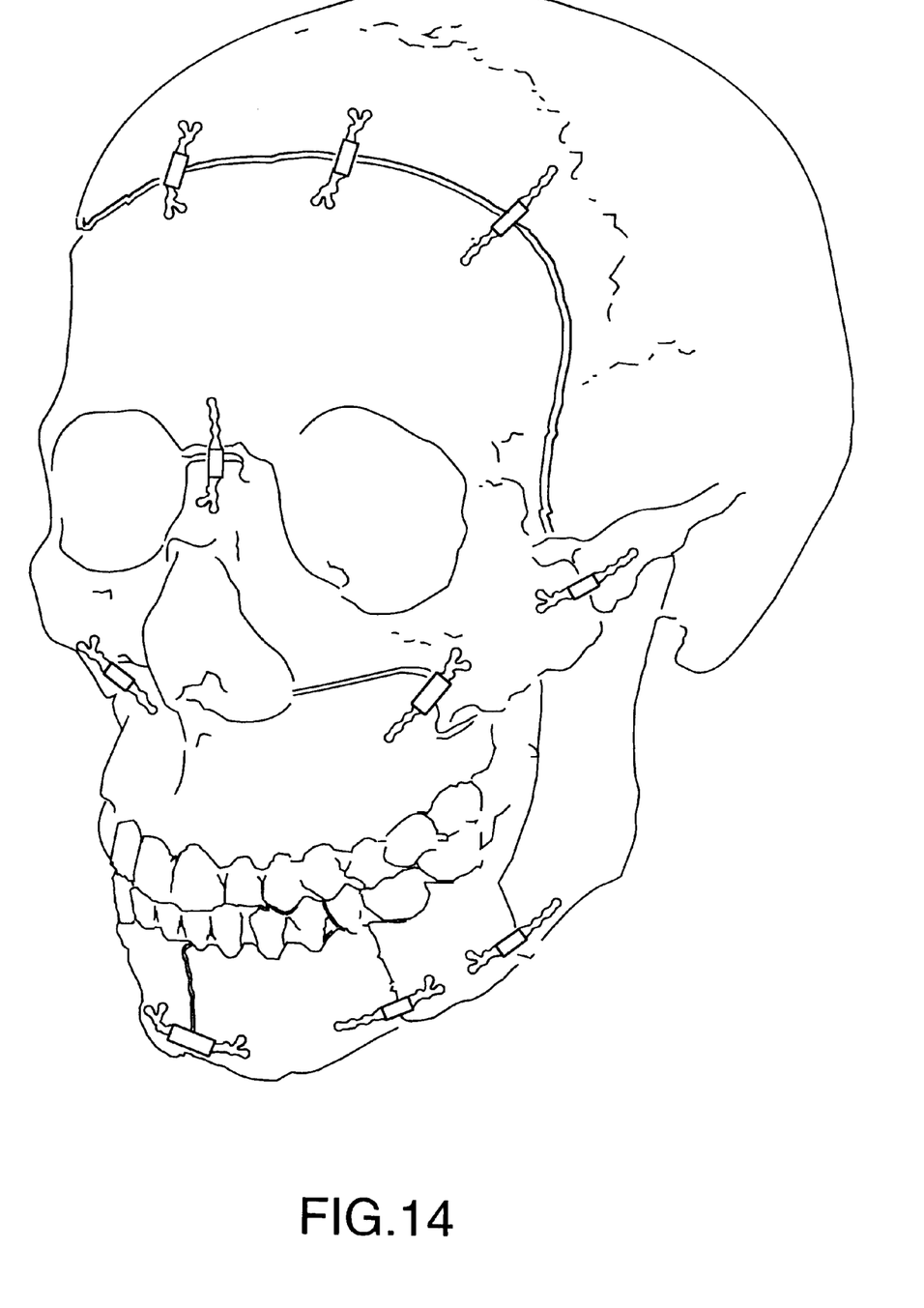
FIG. 14 is a perspective view which shows the telescopic bone plates placed at osteotomy (surgical fracture of the bone) sites in the craniofacial skeleton.
Figure 15:
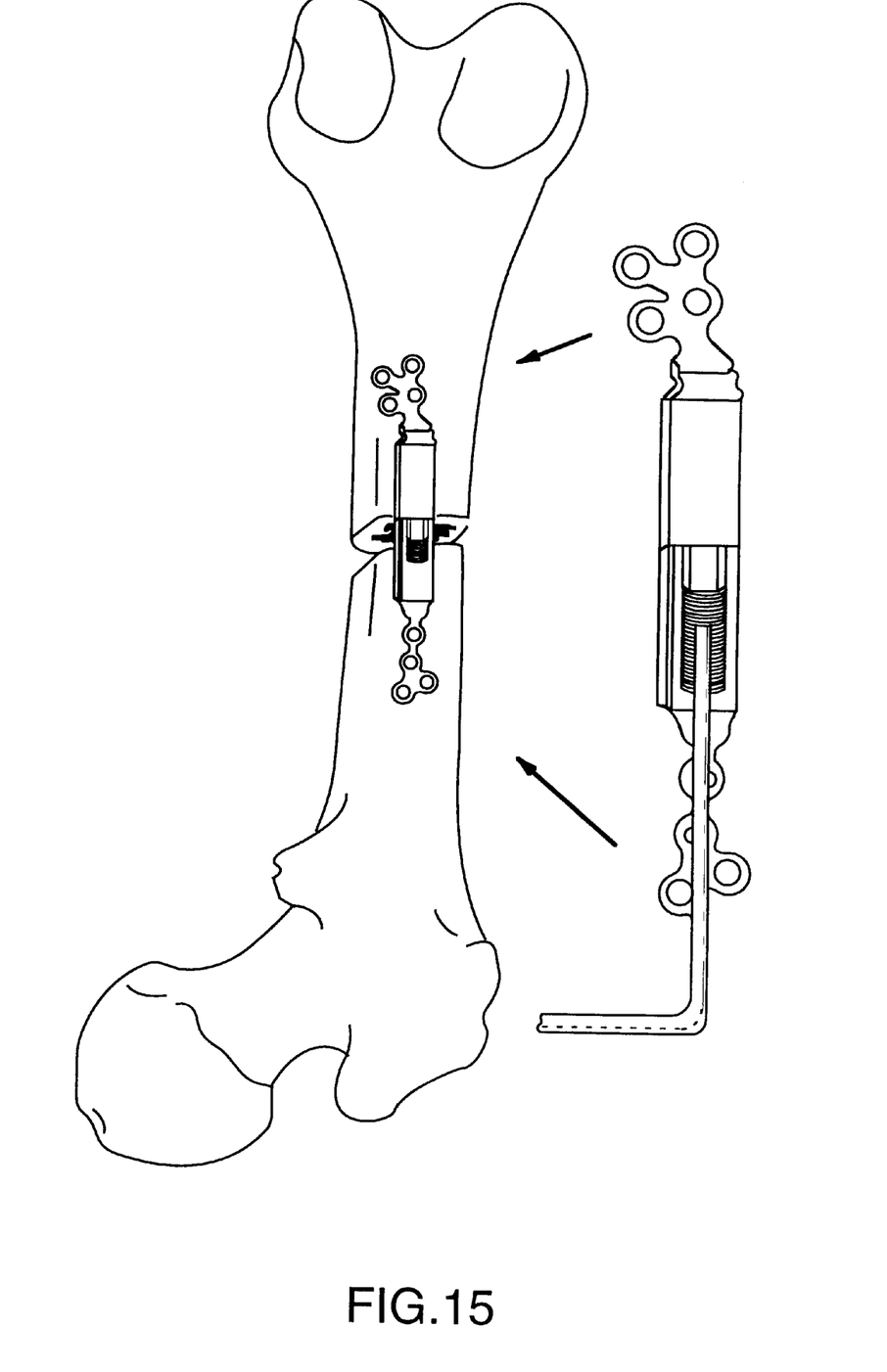
FIG. 15 is a perspective view which shows a telescopic bone plate placed at an osteotomy site in a long bone.

This embodiment of the telescopic bone plate incorporates five new design features which are shown in FIGS. 12 and 13.

1) One end of the 5-44UNF thread screw is elongated to permit easier actuation;
2) There is at least one Jack screw assembly to actuate the telescopic bone plate in a medial lateral plane;
3) There is at least one Jack screw assembly to actuate the telescopic bone plate in a superior inferior plane;
4) The top and bottom bone plates are extended and have more holes for improved stabilization on bone;
5) The top and bottom bone plates are offset relative to the top panel and the bottom panel.

This embodiment allows medial lateral and superior inferior adjustments of the position of the top and bottom bone plates to precisely control osteogenesis. This gives much more variability in the direction in which the bone is being displaced to allow total control of the final position of the distracted mandible. Multi directional adaptability of the vectors of force generated by the device provides greater flexibility for the surgeon because the initial placement of the device becomes less critical. This embodiment utilizes a telescopic means similar to that of the third embodiment, described above, to distract bone in an anterior posterior plane. This part of the telescopic means consists of a unitary casing and a 5-44UNF thread screw 40. The exposed end of the 5-44UNF thread screw 40 with the hexagonal socket 41 is elongated and extends anterior from the telescopic bone plate. This permits easier access to the hexagonal socket 41 of the 5-44UNF thread screw 40. Actuation is with a hexagonal key 60. Since the device is implanted inside the patient, the elongated 5-44UNF thread screw 40 simplifies actuation of the device externally to the patient.

Figure 16:
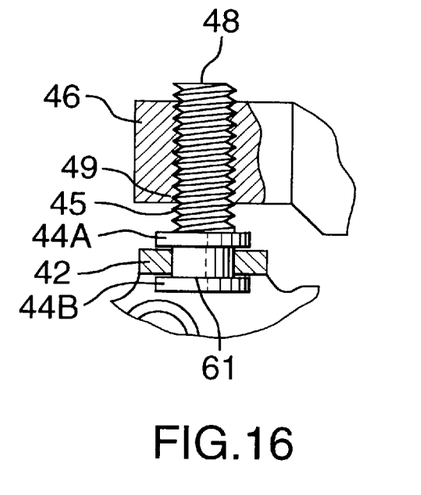
FIG. 16 is a cross sectional view of the posterior Jack screw of the fourth embodiment for superior inferior adjustment of the telescopic bone plate.
Figure 17:
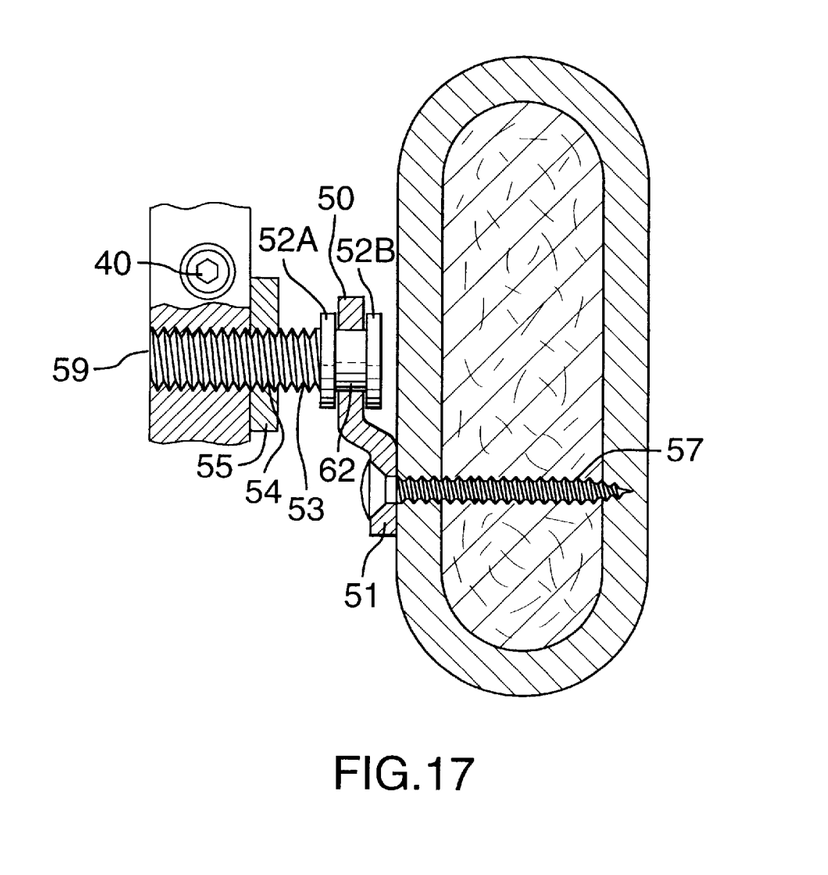
FIG. 17 is a cross sectional anterior view of the anterior Jack screw of the fourth embodiment for medial lateral adjustment of the telescopic bone plate.

This embodiment also has a displacement means at each of its anterior and posterior ends. In a preferred embodiment of the invention, the displacement means is a Jack screw assembly (FIGS. 16, 17). However, it would be clear to one skilled in the art that other displacement means could also be used, such as the 5-44UNF thread screw assembly (telescopic means) described above. The posterior end of the telescopic bone plate has a platform 42 that extends from the top bone plate 43 (FIGS. 12, 16). This platform 42 has an aperture which receives one end of a posterior screw 45. This end of the posterior screw 45 has a smooth, non-threaded rotating surface 61 which is between a first collar 44A and a second collar 44B. This rotating surface 61 is received in the aperture and held in place by the first collar 44A and the second collar 44B (FIG. 16). The smooth, non-threaded rotating surface provides increased stability, rigidity and strength. This design will also lessen the likelihood of the screw coming loose during activation. Additionally, the strength requirements of the entire appliance under activation in different vectors will be borne by the threads of the screw and the threads of the appliance itself. The other end of the posterior screw 45 is received in a stage 46 fixed to the top panel 47. The stage 46 has a threaded aperture 49. The posterior screw 45 has its longitudinal axis in a superior inferior plane. The end of the posterior screw 45 received by the stage 46 has a hexagonal socket 48. A hexagonal key with a right angle offset bend is inserted in the hexagonal socket 48 to turn the posterior screw 45 and move the relative position of the platform 42 and the stage 46 in a superior inferior plane. For example, using the hexagonal key to turn the posterior screw 45 in one direction will separate the platform 42 and the stage 46. Turning the posterior screw 45 in the opposite direction will decrease the distance between the platform 42 and stage 46.

The anterior end of the appliance has a platform 50 that extends from the bottom bone plate 51 (FIGS. 12, 17). This platform has an aperture which receives one end of an anterior screws 53. This end of the anterior screw 53 has a smooth, non-threaded rotating surface 62 which is between a third collar 52A and a fourth collar 52B. This rotating surface 62 is received in the aperture and held in place by the third collar 52A and the fourth collar 52B (FIG. 17). The other end of the anterior screw 53 is received in a threaded opening 54 in a stage 55. The stage 55 is fixed to the bottom panel 56. The anterior screw 53 has it longitudinal axis in a medial lateral plane. The end of anterior screw 53 received by the stage 55 has a hexagonal socket 59. A hexagonal key is inserted in the hexagonal socket 59 to turn the anterior screw 53 and move the relative position of the platform 50 and the stage 55 in a medial lateral plane. For example, using the hexagonal key to turn the anterior screw 53 in one direction will separate the platform 50 and the stage 55. Turning the anterior screw 53 in the opposite direction will decrease the distance between the platform 50 and the stage 55.

This embodiment also has a longer top bone plate 43 and bottom bone plate 51 to allow the use of more screws 57 to attach the device for improved stabilization. The screw holes 58 in the top and bottom bone plates 43, 51 accommodate fastening means, such as 2 mm self tapping screws. Improved stabilization of the telescopic bone plate prevents loosening of the screws and slippage of the device. Improving stabilization makes the telescopic bone plate particularly effective in larger bone systems where greater forces are generated, for example bones of the legs or arms. In these parts, the bones are heavier than those in the face and subject to significant forces by the patient's movements.

The top and bottom bone plates 43, 51 are offset in this embodiment so that they are superior to the top panel and the bottom panel 47, 56. This shift in position simplifies actuation of the device. It also allows the use of top and bottom bone plates 43, 51 that are significantly loner than those of earlier embodiments without increasing the overall length of the telescopic bone plate.

Surgical Technique

The telescopic bone plate for distraction osteogenesis is small and can be placed in an open procedure transorally. The telescopic bone plate can be adapted to individual anatomical contours. The device is designed to be placed and covered sub mucosally. It is accessed through a remote small access site in the mucosa for actuation. Because the plate is completely tissue covered, it offers many advantages over previous distractors. It avoids potential complications including wound dehiscence, chronic ingress or oral bacteria, potential for infection or loosening of the device and further adverse effects on the bony healing during distraction osteogenesis.

In this surgical procedure the osteotomy (surgical fracture of the bone) design used was a sagittal split osteotomy. This provided two broad surfaces of bony interface. Other osteotomy designs that can be used also include body osteotomy or ramus osteotomy. This standard transoral approach to the mandible is utilized as an open procedure. Complete subperiosteal dissection is carried out exposing the lateral aspect of the mandible and the ramus. Medial dissection is carried out enabling a horizontal medial cortex osteotomy to be created. An anterior ramus osteotomy is created as well as a lateral cortex osteotomy. It is advisable at this stage to contour and place the device prior to actual splitting of the mandible. This allows correct orientation of the segments and condylar position. Generally 1–2 screws in either bony segment are placed initially. This provides solid reference for reapplying the bone plate at a later time. The preferred fastening means for stabilizing the plate to the mandible comprises stainless steel 2.0 mm self tapping screws. Initial screw placement is monocortical as initial screws are utilized to temporarily stabilize the appliance in its desired position.

The sagittal split osteotomy (fracture) is completed in the usual fashion with the osteotome technique. Some bony sculpting may be necessary to allow passivity of the segments for antero/postero distraction ostcogenesis. Some degree of muscle stripping is carried out as well to ensure passivity of the segments. The device is then reapplied utilizing the previously drilled holes. The telescopic bone plate is attached to bone using fastening means, such as monocortical or bicortical screws. A depth gauge can be used but the screws should be bicortical in the anterior part of the mandible. In the posterior, the ramus is somewhat thin and essentially as long as the screws are placed in an area that does not interfere with the sliding osteotomy design they can be either monocortical or bicortical. It is recommended that the device be placed at the inferior border of the mandible. Posterior access can be percutaneous through unbroken skin with a small stab incision. The device is placed at the inferior border of the mandible to avoid the inferior alveolar neurovascular bundle and the roots of the teeth. It is advisable to place 3 screws per bony segment. The device should be at its zero position when applied to the mandible. After it is applied to the mandible it is opened 2–4 mm to observe the movement of the bony segments. The device is then closed back to 0 mm, tissues are closed with 2 layer closure in a water tight fashion. A similar procedure is carried out for the contra lateral side of the mandible.

The following is the alternative surgical technique for body ramus osteotomy for distraction osteogenesis of the mandible. A standard incision is made from the anterior mid ramus up to the bicuspid region, care being taken to be out in the vestibule. Sharp dissection is carried out bone to bone. A sub periosteal dissection is carried out exposing the lateral aspect of the ramus. Careful minimal stripping was carried out on the medial aspect of the mandible just distal to the dentition. A location is identified for the osteotomy site. A bony window in the lateral cortex is carefully outlined with a 701 burr and gently removed with an osteotome. This allows exposure of the inferior alveolar neuro-vascular bundle. Once this is identified, a planned area for osteotomy cut can be made.

The telescopic bone plate is contoured to fit the lateral aspect of the mandible. It is important to ensure that the correct vector or alignment of the appliance is achieved such that the vector of distraction is the one desired. Once this is carried out monocortical screws are utilized one to two at either end of the appliance to secure its position. Posterior screws are often placed with a percutaneous trocar due to limited intra oral access.

The appliance is removed and the body ramus osteotomy is completed with a 701 burr. Care is taken to avoid minimal stripping of the mucoperiosteum an the medial aspect of the mandible. The osteotomy is completed with an osteotome. Once the osteotomy is completed the telescopic bone plate can be re-applied utilizing the previously drilled holes. A depth gauge can be utilized to measure appropriate thickness, a minimum of three screws per segment, four to six screws ay be possible in the posterior segment. Wounds are irrigated and closure is recommended with interrupted vertical and/or horizontal mattress sutures with non resorbable suture material.

Actuation can begin between the fourth to seventh day after osteotomy. A small stab incision is made in the anterior portion of the vestibule. Blunt dissection is carried out down to the activating portion of the appliance where the hexagonal key is inserted. The hexagonal key is introduced and under direct visualization is opened 1.1 mm per day until the desired lengthening of bone is achieved.

The appliance would normally be removed three months after distraction is complete. This could be accomplished via trans oral incision with sub periosteal dissection and removal of screws and subsequently appliance. Posterior screws may be removed by percutaneous technique. The surgical site is irrigated and closed with interrupted sutures.

Actuation

Actuation of the telescopic bone plate usually occurs approximately 4–10 days post placement. This allows primary wound healing. A small stab incision with blunt dissection is carried out at the site of the hexagonal socket of the device. A standard hexagonal key is placed into the hexagonal socket and turned to actuate the device in order to longitudinally displace the top bone plate and the bottom bone plate relative to each other by 1.1 mm per day until the desired degree of distraction osteogenesis is carried out. Actuation of the anterior screw through the anterior stab incision is accomplished by using a hexagonal key. One complete revolution of the screw would result in 1.1 mm of distraction. Actuation of the posterior screw would involve a small stab incision superior to the appliance in the posterior region with blunt dissection down to the hexagonal surface. Again, one revolution of the screw would result in 1. mm of distraction. At the completion of actuation no surgical closure of the access holes are needed. The access holes usually heal quite well by secondary intention. Antibiotic prophylaxis is used at the time of placement of the device. The patient must be maintained on a minimal chewing soft diet for 6 weeks post operatively. Monitoring of the occlusion and the degree of distraction via clinical and radiographic means is indicated.

In Vivo Results

The first embodiment of the telescopic bone plate was tested in a primate. A sagittal split osteotomy of the mandible was carried out. Bilateral telescopic bone plates were placed at the right and left osteotomy sites with bone screws. The mucosa was closed to cover the device. Ten days later a window was made in the mucosa exposing the hexagonal socket at the front end of the screw of the device. Actuation by a standard hexagonal key at a rate of 1.1 mm a day was carried out for ten days. At the end of the actuation period, the window in the mucosa was allowed to heal. The mandible was successfully advanced. During the retention period the animal thrived, gained weight and did not present any evidence of infection or scar formation. Histological analysis revealed bony union of the distracted mandible segments.

The second and third embodiments were also tested in a primate. A sagittal split osteotomy of the right side of the mandible and an osteotomy of the ramus of the left side of the mandible was carried out. The second embodiment was placed at the right osteotomy site with bone screws and the third embodiment was placed at the left osteotomy site with bone screws. The mucosa was closed to cover each device. Seven days later a window was made in the mucosa exposing the hexagonal socket at the front end of the screw of each of the devices. Actuation by a standard hexagonal key at a rate of 1.1 mm a day was carried out for 9 days.

At the end of the actuation period, the window in the mucosa was allows to heal. The mandible was successfully advanced and distraction osteogenesis occurred. During the retention period the animal thrived, gained weight and did not present any evidence of infection or scar formation. Histological analysis revealed bony union of the distracted mandibular segments and normal temporomandibular joints.

Alternate Surgical Application

Mid face retrusion is a commonly occurring deformity. Distraction osteogenesis of the anterior maxilla with a telescopic bone plate can be carried out predictably with excellent bone formation and no adverse effects.

Mobilizing the entire maxilla via gradual distraction process is another application of the telescopic bone plate. The maxilla is a membranous bone with numerous vertical walls including the lateral wall of the maxilla, the medial wall of the maxillary sinus, nasal septum and vomer and contra lateral medial sinus wall and lateral maxillary wall. Additionally there is the bony interface between the posterior wall of the maxilla and the pterygoid plates.

Distraction osteogenesis of the maxilla may be utilized at the Le Fort I level. Le Fort I osteotomy including the lateral nasal wall, medial wall, separation of septum and vomer as well as separating the maxilla from the pterygoid plates would be accomplished with subsequent application of intra oral distraction device previously described. Modifications to the device would be necessary based on the anatomical considerations of the maxilla.

The initial osteotomy cuts and placement of the sub mucosal appliance are accomplished. The appliance is exposed at approximately one week post osteotomy cuts and activated 1.1 mm a day for a total of 10 mm of advancement. All surgical procedures are carried out under general anesthesia. Patients are maintained on soft diet minimal chewing during the follow up period.

Evaluation of bony healing in the areas of advancement of the maxilla is accomplished via radiographic analysis, CT Scan, and routine histologic methods previously described.

There are further applications for the telescopic bone plate due to the multi directional actuation. These include:

1. Distraction osteogenesis widening of the mandibular symphysis.
2. Distraction osteogenesis over resected portions of the mandible or maxilla for tumor ablative surgery.
3. Maxillary or mandibular ridge augmentation via distraction osteogenesis.
4. Distraction osteogenesis of the mid face via Le Fort II of Le Fort III osteotomy design.
5. Distraction osteogenesis of the cranial bones.

Variations in design of the appliance accommodate the different anatomical configurations and access would be undertaken.

Material and Manufacturing Methods

The top and bottom panels with their integrated bone plates are manufactured by erosive die sinking and erosive cutting. The thread screw assembly was manufactured by high speed lathe and erosive die sinking. All components were made out of Type 316 stainless steel.

Stainless steel Type 316 is the material for severe corrosive conditions, as it has an exceptional characteristic of corrosion resistance. In addition, good abrasion resistance and cold forming makes it a good choice for this application.

During an electric discharge between two electrodes, material melts and is then "thrown off" by the resultant gas pressure. The working principle of erosive die sinking and erosive cutting machines is based on this discharge. The process is controlled and monitored by the computerized central processor. of the machines and therefore it is possible to obtain apertures and contours of the highest accuracy. Erosive die sinking is a pure reproduction of the shape of the electrode whereas erosive cutting employs an electrolytic copper or brass wire moving over the workpiece surface thus producing a type of "cut".

Specifications for the Telescopic Bone Plate

The specifications of embodiments of the telescopic bone plate are as follows:

|  | First Embodiment | Second and Third Embodiment |
| --- | --- | --- |
| Collapsed length = | 13.00 mm | 13.00 mm |
| Width = | 7.00 mm | 8.00 mm |
| Height = | 4.15 mm | 5.16 mm |
| Weight = | 5 grams | 5.5 grams |
| Expanded length (overall) = | 27 mm | 27 mm |
| Compressive strength (ultimate) = | 1,290 N | 1450 N (tested on expansion screw without bone plates) |
| # of engaged threads = | 5 per side | 5 per side |
| Linear travel = | 1.15 mm/turn | 1.15 mm/turn |

The top and bottom bone plates are 1 mm thick. They can be customized with respect to their design and number of holes to suit the surgical site.

The present invention has been described in terms of particular embodiments found or proposed by the present inventors to comprise preferred modes for the practice of the invention. It will be appreciated by those of skill in the art that, in light of the present disclosure, numerous modifications and changes can be made in the particular embodiments exemplified without departing from the intended scope of the invention. All such modifications are intended to be included within the scope of the appended claims.

All publications, patents and patent applications are herein incorporated by reference in their entirety to the same extent as if each individual publication, patent or patent application was specifically and individually indicated to be incorporated by reference in its entirety.

REFERENCES

1. Bell, W, Proffit W, White R. Surgical correction of dentofacial deformities. Vol 1 Philadelphia: Saunders 1980.
2. Costantino P, Friedma C D. Distraction osteogenesis. Applications for mandibular regrowth. Otolaryugol Clin North Am. 24:1433–1991.
3. Oklund S A, Prolo D J, Gutienez R Y, King S E. Quantitative comparison of healing in cranial fresh autografts and processed autografts and allografts in canine skull defects. Clin Orthop 269–291, 1986.
4. Wolfe S A. Autogenous bone grafts versus alloplastic material in maxillofacial surgery. Clin Plast Surg 9:539–540, 1982.
5. Benoist M. Experience with 220 cases of mandibular reconstruction. J Oral Maxillofac Surg 6:40–49, 1978.
6. Wolford L M, Wardrop R W, Hartog J M Coralliac porus hydroxyapatite as a bone graft substitute in orthognathic surgery. J Oral Maxillofac Surg 45:1034–1042, 1987.
7. Araujo A, Schendel S, Wolford L, Epker B. Total maxillary advancement with and without bone grafting. J. Oral Surg 63:849–1978.
8. Horster W. Experience with functionally stable plate osteosynthesis after forward displacement of the upper jaw. J Maxillofac Surg 8:176–181, 1980.
9. Westwood R, Tilson H. Complications associated with maxillary osteotomies. J Oral Surg 33:104–107, 1975.
10. Bell W, Levy B. Healing after anterior maxillary osteotomy J Oral Surg 28:728–734, 1970.
11. Ilizarov G, Devyatov A, Kamerin V. Plastic reconstruction of longitudinal bone defects by means of compression and subsequent distraction. Acta Chir Plast 22:32–46, 1980.
12. Paley D. Current techniques of limb lengthening, J. Pediatr Orthop 8:73–91, 1988.
13. Sproul J T, Price C T. Recent advances in limb lengthening. Part I. Clinical advances. Orthop Rev 21:307–314, 1992.
14. Simard S, Marchant M, Mencio G. The Ilizarov procedure: Limb lengthening and its implications. Phys Ther 72:25–34, 1992.
15. Orbay J L, Frankel V H, Finkle J E, Kummer F J. Canine leg lengthening by the Ilizarov technique. Clin Orthop 278:265–273.
16. DeBastiani G, Aldegheri R, Renzi-Brivio L, Trivella G. Limb lengthening by callous distraction (callotasis). J Pediatr Orthop 1987.
17. Kujimoto H, Yasui N, Goto T, Matsuda S, Yutaka S. Bone lengthening in rabbits by callus distraction. J Bone Joint Surg Br 70:543–549, 1988.
18. Aldegheri R, Renzi-Brivio L, Agostini S. The callotasis method of limb lengthening. Clin Orthop 241:37–45, 1989.
19. White S H, Kenwright J. The time of distraction of an osteotomy. J Bone Joint Surg Br 72:356–361, 1990.
20. Price T C, Mann J W. Experience with the Orthofix device for limb lengthening. Clin Orthop 22:651–661, 1991.
21. Ilizarov G A. Clinical application of the tension-stress effect for limb lengthening. Clin Orthop 250:8–26, 1990.
22. Cattaneo R, Villa A, Catagni M A, Bell D. Lengthening of the humerus using the Ilizarov technique. Clin Orthop 250:117–124.
23. Villa A, Paley D, Catagni M A, Bell D, Cattaneo R. Lengthening of the forearm by the Ilizarov technique. Clin Orthop 250:125–1990.
24. Paley D. Problems obstacles and complications of limb lengthening by the Ilizarov technique. Clin Orthop 250:81–103, 1990.
25. Altuna G, Walker D A, Freeman E. Surgically assisted rapid orthodontic lengthening of the maxilla in primates—A pilot study. Am J Orthodtofac Orthop 107:531–536, 1995.
26. Snyder C C, Levine G A, Swanson H M, Browne E Z Jr. Mandibular lengthening by gradual distraction. Plast Reconstr. Surg 51:506–508.
27. Constantino P D, Shybut G, Friedman C D, et al. Segmental mandibular regeneration by distraction osteogenesis. Arch Otolaryngol Head Neck Surg 1163:535–545, 1990.
28. Constantino P D, Friedman C D. Distraction osteogenesis, applications for mandibular regrowth. Otolaryngol Clin North Am 24:1433–1443, 1991.
29. Costantino P D, Friedman C D, Shindo M L, et al. Experimental mandibular regrowth by distraction osteogenesis—Long-term results. Arch Otolaryngol Head Neck Surg 119:551, 1993.
30. McCarthy J G, Schreiber J, Karp N, Thorne C H, Grayson B H. Lengthening the human mandible by gradual distraction. Plast Reconstr Surg 89:1–8, 1992.
31. Karp S N, Thorne C H M, McCarthy J G, Sissons H A. Bone lengthening in the craniofacial skeleton. Ann Plast Surg 24:1990.
32. Karp S N, McCarthy J G, Schreiber S S, Hubert A S, Throne C H M. Membranous bone lengthening: A serial histological study. Ann Plast Surg 29:2–7, 1992.
33. Gantous A, Phillips J H, Catton P, Holmberg D. Distraction osteogenesis in the irradiated canine mandible. Plast Reconstr Surg 93:164–1668, 1994.
34. Komura Y, Takato T, Harii K, Yonemara Y. The histologic analysis of distraction osteogenesis of the mandible in rabbits. Plast Reconstr Surg 94:152–158, 1994.

35. Moor I I M, Guzman-Stein G, Proudman T W, Abbott A H, Netherway D J, David D J. Mandibular lengthening by distraction for airway obstruction in Treacher-Collins syndrome. J Craniofac Surg 5:22–25, 1994.
36. Snyder C C, Levine G A, Swanson H M, Browne E Z. Mandibular lengthening by gradual distraction. Plast. Reconstru Surg 5:506–1973.
37. Altuna G, Walker D A, Freeman E. Rapid orthopedic lengthening of the mandible in primates by sagittal split osteotomy and distraction osteogenesis: A pilot study. Int J Adult Orthod Orthognath Surg 10:59–64, 1995.
38. Altuna G, Walker D A, Freeman E. Surgically assisted rapid orthopedic lengthening of the maxilla in primates. Relapse following distraction osteogenesis. Int. J. Adult Orthod Orthognath Surg 1995 (10:269–275, 1995)
39. Tschakaloff A, Losken H, Mooney M, Sregel M et. al. Internal calvarial bone distraction in rabbits with experimental coronal suture immobilization. J Craniofacial Surg 5:5 318–325, 1994.
40. Molina F, Monasterio F. Mandibular elongation and remodeling by distraction: Farewell to major osteotomies Plastic and Reconstructive Surg 96:825–840, 1995.
41. McCarthy J, Staffenberg D, Wood R, Cutting C, Grayson B, Thorne C, Introduction of an Intra oral bone lengthening device, Plastic and Reconstructive Surgery 96:978–981, 1995.
42. Chin M, Toth B. Distraction osteogenesis in maxillofacial surgery using internal devices J. Oral & Maxillofac. Surg 54:45–53, 1996.

What is claimed is:

1. A telescopic bone plate for distracting osteotomically separated bone sections, the telescopic bone plate having a longitudinal axis and a lateral axis and comprising:
    a top bone plate and a bottom bone plate adjustable relative to each other in at least a superior inferior direction substantially perpendicular to both the longitudinal axis and the lateral axis of the telescopic bone plate, and including means for fastening the telescopic bone plate to bone, at least one displacement means to adjust the positions of the top bone plate and bottom bone plate relative to each other, said displacement means including telescopic means which is actuated in a superior inferior plane, and
    wherein the displacement means is able to be actuated internally to a patient.
2. The telescopic bone plate of claim 1, wherein the displacement means is configured for actuation intraorally.
3. The telescopic bone plate of claim 1, wherein the top bone plate and the bottom bone plate are further adjustable relative to one another in a medial lateral direction and substantially parallel to the lateral axis of the telescopic bone plate wherein said displacement means further comprises a telescopic means which is actuated in a medial lateral plane.
4. The telescopic bone plate of claim 1, wherein the top bone plate and the bottom bone plate are further adjustable relative to each other in an anterior posterior direction, substantially parallel to the longitudinal axis of the top telescopic bone plates, and wherein said displacement means further comprises a telescopic means which actuates the top bone plate and the bottom bone plate in an anterior posterior direction.
5. The telescopic bone plate of claim 1, wherein the top bone plate further comprises a top panel and the bottom bone plate further comprises a bottom panel, wherein the top panel overlays the bottom panel and wherein the telescopic means is located between the top panel and the bottom panel.
6. The telescopic bone plate of claim 1, further comprising a casing for the telescoping means of the bone plate.
7. The bone plate of claim 1, wherein the displacement means is a Jack screw assembly.
8. The bone plate of claim 7, wherein the Jack screw assembly is adapted for actuation intraorally using a control means located outside the patient's body.
9. The bone plate of claim 7, wherein the Jack screw assembly is adapted for actuation internally to the patient using a control means located outside the patient's body.
10. A telescopic bone plate for distracting osteotomically separated bone sections, the plate comprising:
    a top bone plate and a bottom bone plate adjustable relative to each other in at least one of three mutually perpendicular directions: a medial lateral direction, a superior inferior direction and an anterior posterior direction, and including means for fastening the telescopic bone plate to bone, at least one displacement means to adjust the positions of the top bone plate and the bottom bone plate relative to each other, wherein the displacement means is actuated internally to a patient, and is actuated by a motor.
11. The telescopic bone plate for distracting osteotomically separated bone sections, the telescopic bone plate having a longitudinal axis and a lateral axis and comprising:
    a top bone plate and a bottom bone plate adjustable relative to each other in at least one of a medial lateral direction substantially parallel to the lateral axis of the telescopic bone plate, and a superior inferior direction substantially perpendicular to the both the longitudinal axis and the lateral axis of the telescopic bone plate, and including means for fastening the telescopic bone plate to one, at least one displacement means to adjust the positions of the top bone plate and the bottom bone plate relative to each other, wherein the displacement means is able to be actuated internally to a patient.
12. The telescopic bone plate of claim 11, wherein the telescopic means is configured for actuation intraorally.
13. The telescopic bone plate of claim 11, wherein the displacement means is actuated on a plane that is substantially the same plane as a plane of the top bone plate or bottom bone plate.
14. The telescopic bone plate of claim 11, wherein the top bone plate and the bottom bone plate have planar surfaces and are adjustable relative to each other in said medial lateral direction, substantially perpendicular to the planar surfaces of the top and bottom bone plates and wherein said displacement means comprises a telescopic means which actuates the top bone plate and the bottom bone plate in a medial lateral plane.
15. The telescopic bone plate of claim 11, wherein the displacement means is actuated in the superior inferior plane substantially perpendicular to both the longitudinal axis and lateral axis of the telescopic bone plate.
16. The telescopic bone plate of claim 11, wherein the displacement means actuates the top bone plate and the bottom bone plate in the medial lateral direction substantially parallel to the lateral axis of the telescopic bone plates.
17. The bone plate of claim 11, wherein the displacement means is a thread screw assembly.
18. The bone plate of claim 17, wherein the thread screw assembly is adapted for actuation intraorally using a control means located outside a patient's body.
19. The bone plate of claim 17, wherein the thread screw assembly is adapted for actuation internally to the patient using a control means located outside the patient's body.
20. The telescopic bone plate of claim 11, wherein the bone plate has a compressive strength of at least 1,290N.

21. The telescopic bone plate of claim 11, wherein the bone plate has a profile in a superior inferior direction substantially perpendicular to both the longitudinal axis and lateral axis of the telescopic bone plate of less than 6 mm.

22. The telescopic bone plate of claim 11 or claim 2, wherein one of the bottom bone plate and the top bone plate is inclined relative to the other.

23. The telescopic bone plate of claim 11 or claim 2, wherein at least one of said top bone plate and said bottom bone plate have holes therethrough, and one or more slits between the holes to facilitate the contouring and fastening of the at least one of said top bone plate and said bottom bone plate to the bone.

24. The telescopic bone plate of claim 11, wherein the adjustable distance between the top bone plate and the bottom bone plate is at least 10 mm.

25. The telescopic bone plate of claim 11 or claim 1, wherein the displacement means is actuated by a motor.

26. A telescopic bone plate for distracting osteotomically separated bone sections telescopic bone plate having a longitudinal axis and a lateral axis and comprising:

a top bone plate and a bottom bone plate adjustable relative to each other in at least two of a medial lateral direction, substantially parallel to the lateral axis of the telescopic bone plate, a superior inferior direction substantially perpendicular to both the longitudinal axis and the lateral axis of the telescopic bone plate, and an anterior posterior direction, substantially parallel to the longitudinal axis of the telescopic bone plate and including means for fastening the telescopic bone plate to bone, at least two displacement means for adjusting the positions of the top bone plate and the bottom bone plate relative to each other in at least two of three mutually perpendicular planes a medial lateral plane, a superior inferior plane, and an anterior posterior plane.

27. A telescopic bone plate according to claim 26, including three displacement means for adjusting the relative positions of the top bone plate and the bottom bone plate to each other in said medial lateral plane, said superior inferior plane and said anterior posterior plane.

28. A telescopic bone plate of claim 26, for implantation is an oral cavity, wherein the displacement means are configured for location in said oral cavity.

29. A telescopic bone plate of claim 28, further including actuating means for actuating the displacement means to adjust the relative positions of the top and bottom bone plates, the actuating means being coupled to the displacement means and being locatable in said oral cavity.

30. The telescopic bone plate for claim 26, wherein a first one of said displacement means is a telescopic means which is actuated in an anterior posterior plane substantially parallel to the longitudinal axis of the telescopic bone plate.

31. The telescopic bone plate of claim 26, wherein a first one of said displacement means is actuated in a superior inferior plane substantially perpendicular to both the longitudinal axis and lateral axis of the telescopic bone plate.

32. The telescopic bone plate of claim 26, wherein a first one of said displacement means is actuated in a medial lateral plane substantially parallel to the lateral axis of the telescopic bone plate.

33. The telescopic bone plate of claim 26, wherein the top bone plate further comprises a top panel and the bottom bone plate further comprises a bottom panel, wherein the top panel overlays the bottom panel and wherein a first one of said displacement means is located between the top panel and the bottom panel.

34. The bone plate of claim 26, including a control means locatable outside of a patient's body for actuating the displacement means to adjust the relative positions of the top and bottom bone plates relative to one another.

35. The telescopic bone plate of claim 26, wherein the bone plate has a profile in the superior inferior direction substantially perpendicular to both of the longitudinal axis and lateral axis of the telescopic bone plate of less than 6 mm.

36. The telescopic bone plate of claim 26, wherein one of the bottom bone plate and the top bone plate is inclined relative to the other.

37. The telescopic bone plate of claim 26, wherein the adjustable distance between the top and the bottom bone plates is at least 10 mm.

38. The telescopic bone plate of claim 26, wherein the displacement means are actuated by a motor.

39. The telescopic bone plate of claim 27, wherein one of the bottom bone plate and the top bone plate is inclined relative to the other.

* * * * *